United States Patent

Viebach et al.

Patent Number: 5,078,124
Date of Patent: Jan. 7, 1992

[54] LITHOTRIPTER KINEMATICS

[75] Inventors: Thomas Viebach, Paehl; Peter Buchbauer, Garching, both of Fed. Rep. of Germany

[73] Assignee: Dornier Medizintechnik GmbH, Munich, Fed. Rep. of Germany

[21] Appl. No.: 513,613

[22] Filed: Apr. 24, 1990

[30] Foreign Application Priority Data

May 11, 1989 [DE] Fed. Rep. of Germany ....... 3915383

[51] Int. Cl.$^5$ .............................................. A61B 17/22
[52] U.S. Cl. ............................ 128/24 OEL; 128/660.03
[58] Field of Search ............ 128/24 A, 24 EL, 660.03

[56] References Cited

U.S. PATENT DOCUMENTS

| | | | |
|---|---|---|---|
| 4,669,483 | 6/1987 | Hepp et al. | 128/24 EL |
| 4,763,652 | 8/1988 | Brisson et al. | 128/24 EL |
| 4,796,613 | 1/1989 | Heumann et al. | 128/24 EL |
| 4,821,729 | 4/1989 | Makofski et al. | 128/24 EL |
| 4,821,730 | 4/1989 | Wurster et al. | 128/24 EL |
| 4,823,774 | 4/1989 | Grasser | 128/24 EL |
| 4,877,017 | 10/1989 | Hahn et al. | 128/24 EL |
| 4,896,673 | 1/1990 | Rose et al. | 128/24 EL |

FOREIGN PATENT DOCUMENTS 0286170  10/1988  European Pat. Off. ....... 128/24 EL

Primary Examiner—Lee S. Cohen
Assistant Examiner—Krista M. Pfaffle
Attorney, Agent, or Firm—R. H. Siegemund

[57] ABSTRACT

A lithotripter includes a therapeutic head with a source for the production and focusing of shockwaves into the body of a patient and is mounted such that a center axis of the head is forced to move and remain on the surface of a cone whose apex point coincides with the focus of the therapeutic head, external to the head, so as to obtain isocentric motion of the head vis-a-vis that focus, even if that focus is made to be positioned in the body of the patient and an ultrasonic transducer is isocentrically mounted on the therapeutic head.

6 Claims, 2 Drawing Sheets

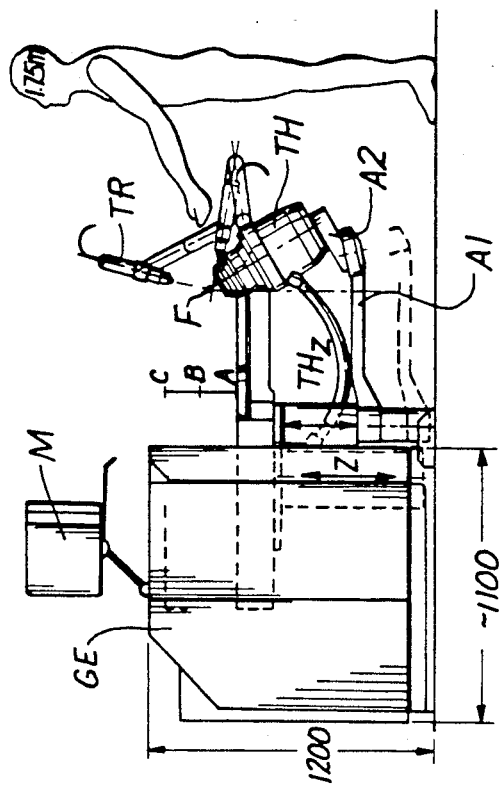
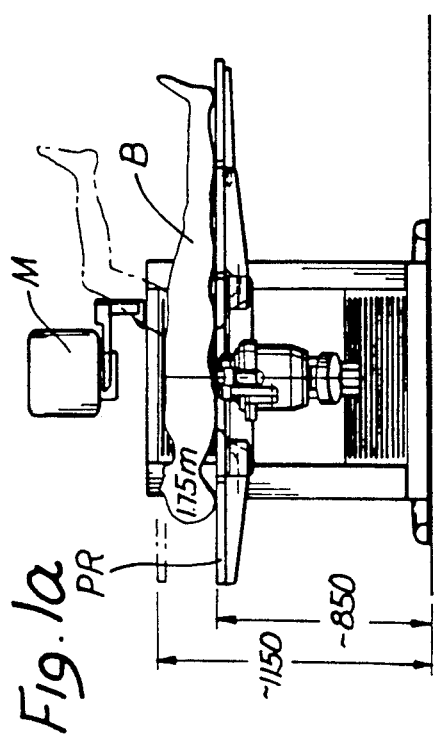
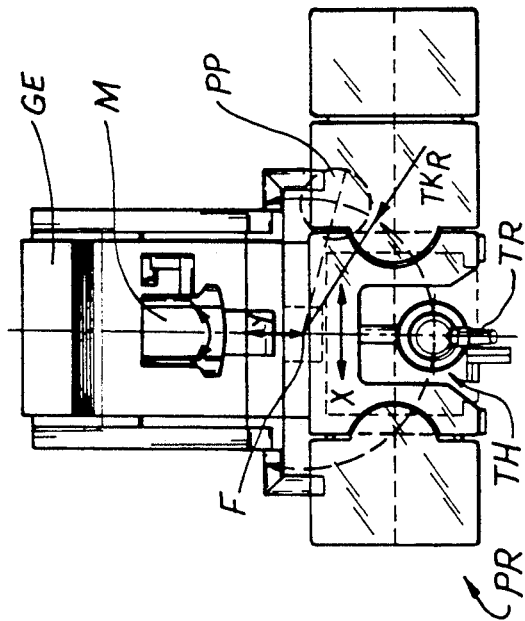

LITHOTRIPTER KINEMATICS

BACKGROUND OF THE INVENTION

The present invention relates to a lithotripter and more generally to apparatus for treating a patient with focused shockwaves under utilization of a therapeutic head which includes structure for the production focusing and conducting of shockwaves in relation to the body of a patient.

Lithotripters i.e. apparatus for contactfree comminution of concrements in the body of a living being include often a stationary shockwave source generator and the position of the patient is shifted, while he or she is on a rest, until the particular body parts that such as kidney with concrements, are situated in the focal point of the shockwave system. In addition other equipment is known wherein the shockwave system that includes a therapeutic head can be positioned in relation to the patient or to each other. Obviously the amount and kind of motion that has to be accommodated is complex while on the other hand the more parts are movable the greater is the degree of freedom as far as positioning is concerned. It is, therefore, a problem to establish a proper relation between ease of operation and adjustability and movability of the patient and as well as to the construction of items of equipment in relation to each other so that it is adequate for the therapeutic purposes on one hand, while on the other hand unnecessary mechanical complexity is to be avoided for reasons of cost maintenance and so forth.

DESCRIPTION OF THE INVENTION

It is an object of the present invention to provide a new and improved apparatus for positioning lithotripter equipment in relation to a patient for purposes of locating a concrement as well as comminution treatment.

It is a specific object of the present invention to provide a new and improved lithotripter that includes a therapeutic head containing structure for the production, focusing and conduction of shockwaves in relation to a suitably positioned patient.

In accordance with the preferred embodiment of the present invention it is suggested to mount the therapeutic head in such a manner that the axis of the head can be moved on a cone having an apex that as given by the external focus of the shockwave equipment so that in fact an isocentric movement is obtained. In the preferred form the cone surface should include a vertical line. In other words the therapeutic head is caused to turn and rotate about its focal point such that the head can be positioned to be on a straight vertical axis or offset axis with a maximum angle being that of a cone angle. The positioning must be obtained even though there is no fastening equipment at the apex point of the cone; the apex point is the focal point which is made to coincide with a point in the interior of a patient. The motion moreover is to be carried out in that upon moving the head on that cone it is also turned so that with reference to the entire equipment it will not rotate about its own longitudinal axis. This is an important feature since it prevents undesirable displacement or shifting of the equipment during the locating as well as comminution procedures locating a concrement is not only carried out in advance of the therapeutic lithotripter treatment, but throughout in an interspersing fashion in order to track the progress of the comminuting.

As far as the practical configuration is concerned the therapeutic head is hinged or linked to a two arm lever whereby the first lever arm is and remain in horizontal and has in one of its end a journal mount for the second arm whose axis of pivoting or turning is at an angle to a vertical, that angle is somewhere between above 0 and 45 degrees. In the preferred form the angle is 15 degrees; and it should not be smaller than 10 and should not exceed 30 for practical purposes. Whenever the angle between the main axis of the therapeutic head and the aforementioned axis of turning of the two arms to each other has the same angle then inherently a cone obtains with an apex angle of 30 degrees. This is the preferred form of practicing the invention.

The entire head including its mounting and moving structures should be provided such that it can be, so to speak, shifted or placed out of the way. This may obtain in that the first arm is made to turn around a vertical axis. This way the entire cone of the therapeutic head can be moved out of the way such that the attending physician has a greater degree of freedom with regard to his position vis-a-vis the patient. Also the equipment as a whole (other than the lithotripter head) may then be used for other related medical treatments such as endourological or transurethral procedures.

In a particular configuration an ultrasonic, locating and imaging transducer is connected to the therapeutic head. The center axis of that transducer is always oriented towards the focal point of the therapeutic head which, as already said, is the apex point of the cone for the displacement and positioning of the therapeutic lithotripter head. Through particular guiding and motion structure one can achieve this result that has the advantage that the focal point is always situated on the center axis of the ultrasonic image. This invariance facilitates greatly the locating procedure. The attending physician will have a relatively large degree of freedom to select for an appropriate window as far as imaging some interior part of the patient is concerned, while at the same time he is certain that he will not lose the focus that is always oriented to the center. Details of this kind of arrangement is disclosed and claimed in our companion application, (Ser. No. 513,612 filed 04/24/1990) and whose content is incorporated by reference.

The ultrasonic transducer is preferably mounted on a ring for rotation on and around the therapeutic head so that rotation obtains around the longitudinal axis of the therapeutic head. The isocentric motion of the transducer will be enforced by a multilever arrangement wherein the first and the third lever are interconnected to be always in parallel. In addition the transducer will be capable of shifting along its longitudinal axis in order to accommodate different distances between the equipment, the patient and the relative location of the concrement. The transducer can also be rotatable about the own axis so that the search for concrement is facilitated further.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIGS. 1a, b, c are respectively front view, side view and top elevation of a lithotripter generally with kinematics in accordance with the preferred embodiment of the present invention.

Proceeding now to the detailed description of the drawings, FIG. 1 illustrates a lithotripter wherein the character GE refers to equipment generally such a power supply and so forth but having in addition a patient rest PR arranged in a cantilever arrangement sideways as can be seen from FIGS. 1a, c. The patient is shown only in FIG. 1a and 2. Details of this kind of rest is disclosed in copending application of common assignee, (Ser. No. 513,612 filed 04-24-1990), whose content is incorporated by reference. There is a therapeutic head TH provided which includes a lithotripter proper such as submerged arc discharge or the like, for the generation of shockwaves. A rotational ellipsoidal reflector with two foci is included; one focus coincides with the discharge locus, the other one is the external lithotripter focus into which concrement comminuting shockwaves are concentrated. An appropriate water cushion means is provided for coupling this reflection structure to the body B of a patient.

Figure 2:
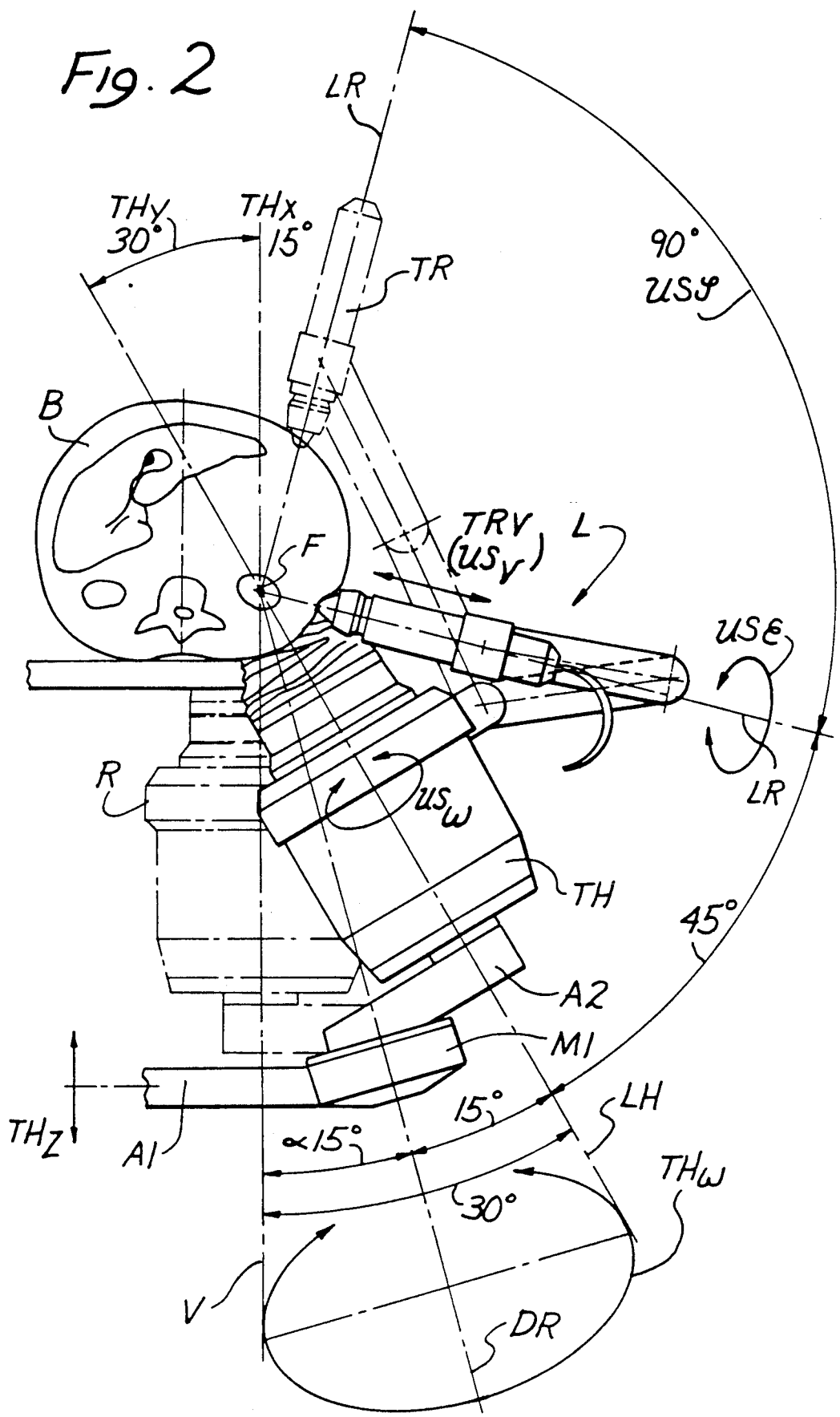
FIG. 2 illustrates the kinematic mounting of the therapeutic head together with the transducer in accordance with the preferred embodiment of the present invention for practicing the best mode thereof.

The patient's rest PR can be moved up or down which situates the entire equipment of the head TH in the vertical (z). The head TH is mounted on a lever structure which includes a cantilever arm A1 which can be moved also in the vertical, independently from the patent rest PR. this motion and adjustability is indicated by THZ. The arm A1 has pivotally mounted on its free end a second arm A2 which carries the head TH in a manner described more fully below. The head TH in turn carries a transducer TR fastened thereto so that the ultrasonic transducer TR has always its center line coincide with the focal point F of the head TH. M is a monitor which displays the ultrasonic image.

FIGS. 1a, b, c illustrate the degrees of freedom for movement particularly of the rest PR. The direction Z which is the vertical was already mentioned and the therapeutic head TH is correspondingly but independently movable in that direction, THZ. The rest may be movable and adjustable further in the horizontal plane i.e. in x and y directions whereby the x axis is generally the longitudinal axis of the rest and will more or less coincide with the length axis of the patient, while the y direction is simply orthogonal to the vertical and to the longitudinal axis as defined.

The therapeutic head TH moreover can be pivoted as is shown in FIG. 1c about the vertical axis in order to assume what may be called a parking position PP which in fact is totally out of the way, and will not interfere with the attending doctor when wanted to check the patient, unimpeded by any equipment. The shifting of the patient's rest in the z-direction is in effect a vertical shifting of the cantilever mount of the rest on the equipment GE. There is shown e.g. a particular maximum height position being e.g. 1.15 m. A normal or usual level of treatment which is illustrated in the figure is about to be 85 cm.

FIG. 1b illustrated three basic levels, A is the placement level for the patient to be placed onto the rest PR. B is the level to which the rest is lifted for lithotriptic treatment and C is the level in which kidney stones usually appear when the rest is in the B-level.

FIG. 2 illustrates the motion of the head TH. The longitudinal axis LH of the head TH can be moved to run on a cone whose apex point coincides with the focal point F of the shockwave focusing system. As shown in our parallel copending application this point F also will coincide with the isocenter of the transducer TR. In the particular embodiment shown in FIG. 2 lithotriptic treatment head TH is fastened to the two levers A1 and A2 shown already in FIG. 1b. Herein arm A2 is mounted to A1 (mount M1) and turns about a fixed axis DR which is the center axis of the cone which the axis LH outlines when the head TH undertakes a conical position movement and adjustment about axis DR. The angle of the axis DR vis-a-vis the vertical is 15 degrees, that means the apex angle of the cone is 30 degrees. The longitudinal axis of the head TH has the same angle, namely 15 degrees vis-a-vis the axis DR. That means that in a certain adjustment position the axis LH of the therapeutic head TH will coincide with the vertical V.

Generally speaking there are basically two motions involved. One is described by the angle TH omega which is in effect the wobbling motion on a cone when the axis LH rotates about the axes DR. In addition the entire arrangement can shift up and down indicated by the vertical movement THZ (see FIG. 1b). Owing to the pivot motion around the cone apex F the head can be moved vis-a-vis the x,y direction by the components THx and THy maximum in each instance 30 degrees (FIG. 2). The component THx is in the x direction as defined in FIG. 1a, that is along side the equipment, in the direction of the length extension of the rest PR which is in a vertical plane transverse to the plane of the drawing of FIG. 2. The shift THy in the y-direction is as far as swiveling of head TH is concerned in the plane of the drawing of FIG. 2, and towards and away from the equipment GE.

The arm A2 has, of course, an angle of extension of 30 degrees vis-a-vis the horizontal extension of arm A1, while the mount M1 establishes the 15 degrees axis DR. Now, as arm A2 rotates about axis DR, through e.g. chains or belts a journal motion is transmitted upon the head TH as it is mounted on the free end of arm AZ such that the orientation of the head TH remains invariant. By way of example the head TH is shown in a position of maximum angular deflector THy out of the vertical V. the levers L and transducer TR extend fully sideways. Now, as lever A2 turns in mount M1 on axis DR, there is an offset motion of the head TH about its axis LH in the journal mount M1 such that the lateral orientation of the lever L to the right remains as shown.

As shown in our copending application Ser. No. 513,612, filed 04-24-1990 whose content is incorporated by the reference the therapeutic head TR is kinematically linked to the head TH, in that three arms (or groups of arms) connect to a ring R on the head TH and to the ultrasonic transducer TR. There is, therefore, made possible a motion of the transducer TR around the axis LH of the therapeutic head TH, there is also made possible a pivot motion of the transducer TR by an angle U.S. phi about an axis that runs normally to the longitudinal axis LH of the head TH through focal point F. There is an angle U.S. omega which is a turning motion of the head TH around its longitudinal axis, and there is a turning motion of the transducer TR itself about its axis LR, which motion is indicated by U.S. epsilon. Then there is the shifting motion TRV in and along the longitudinal axis LR of the transducer TR.

Concerning these various motions, the equipment includes electronic positioning transducers and path tracking devices of known configuration. They are provided to ascertain, on a given scale and in each instance where the various parts are in relation to each other as far as angular and linear positions are concerned and this can be translated into images of points or the like in the ultrasonic image as displayed by the monitor M.

It is readily understandable that the movability of the therapeutic head TH in relation to the patient's rest PR, and the equipment generally, and the moving of the ultrasonic transducer TR in relation to the head TH permits the attending physician to have available a large range of choices as far as viewing angles and treatment windows are concerned combined with the underlying certainty that there is a fixed point F in relation to all, relevant pieces of the equipment that have to cooperate for locating and comminuting concrements.

SUMMARY OF MOTION

Patient rest: vertical-z; horizontal longitudinal-x; horizontal transverse-y;

Head TH vertical THz; horizontal-through-swivel THy; THx (transverse to plane to FIG. 2); turning motion of arm A2 and axis LH about a cone axis DR with F as an apex;

Transducer TR turning by ring R about axis LH-angle U.S. omega; turning about axis LR, angle U.S. epsilon; up/down swivel about F-angle U.S. phi; towards/away from focus F on axis LR-U.S. nu angle.

The invention is not limited to the embodiments described above but all changes and modifications thereof, not constituting departures from the spirit and scope of the invention, are intended to be included.

We claim:

1. A lithotripter including a therapeutic head with a source for the production of shockwaves, and including a structure for focusing and for conduction of shockwaves into the body of a patient, there being a focal point (F) accordingly, the lithotripter further including stationary support structure, the improvement comprising, a mounting structure for the therapeutic head including (a) a first lever extending essentially horizontally from said stationary support structure, (b) a mount on one end of the first lever, (c) a second lever rotatably mounted on the said mount for turning on an axis (DR), said axis (DR) inclined by a particular angle in relation to a vertical line (V) running through the focal point and said axis (DR) being coincident with a central axis of a conical surface, so that a center axis (LH) of the head is forced to move on said conical surface whose apex point coincides with the focal point (F) of the therapeutic head, said focal point being external to the head, as said second lever rotates on the mount of the first lever, an isocentric motion of the head vis-a-vis said focal point is obtained, even if said focal point is made to be positioned in the body of the patient, the conical surface pertaining to a cone having an apex angle between 20 degrees and 30 degrees, and said head being turned as the second lever is being turned, so that with reference to the first lever the head will not rotate and its orientation remains invariant.

2. Apparatus as in claim 1 wherein said conical surface includes said vertical line (V), such that the axis (DR) of rotation is inclined relative to said vertical line (V) by half of the apex angle.

3. Apparatus as in claim 1, including break means for stopping and arresting the position of the therapeutic head once adjusted.

4. Apparatus as in claim 1 including an isocentrically disposed transducer for ultrasonic imaging, wherein the center of said transducer coincides with said apex point and said focal point.

5. A lithotripter comprising a therapeutic head having a center axis (LH) including a shockwave generator constructed for focusing shockwaves in a focal point F external to the generator there being a stationary structure;

first means for mounting the therapeutic head including a stationary lever mounted to the stationary structure, and a turning lever rotating on the stationary lever that is mounted to said stationary structure, the turning lever being provided for mounting said head for rotation about an axis DR that runs through said focal point, said axis (DR) being coincident with a central axis of a conical surface, such that said center axis (LH) of the head rotates about the axis DR of rotation, the center axis (LH) of the head runs through said focal point (F) and the center axis (LH) of the head delineates said conical surface pertaining to a cone with an apex at said focal point (F) wherein the head retains its as it rotates on the conical surface orientation and does not rotate in an absolute sense relative to said stationary lever;

an imaging ultrasonic transducer having an axis (LR); and second means for mounting said imaging transducer on said head in variable positions such that the axis (LR) of the transducer always runs through said focal point (F).

6. A lithotripter as in claim 5, the second means for mounting including a ring having a central axis coinciding with the axis (LH) for rotating the transducer about the head, and lever means for pivoting the transducer about axis (U.S. phi) that runs transversely to said axis (LH).

* * * * *